United States Patent [19]

Tuthill et al.

[11] 4,053,979

[45] Oct. 18, 1977

[54] SUTURE CUTTER

[75] Inventors: Harlan L. Tuthill, Tuxedo Park, N.Y.; John O. Freeborn, New Fairfield, Conn.

[73] Assignee: International Paper Company, New York, N.Y.

[21] Appl. No.: 643,667

[22] Filed: Dec. 23, 1975

[51] Int. Cl.² ............................................. A61B 17/32
[52] U.S. Cl. ...................................... 30/124; 128/305; 128/318
[58] Field of Search ............... 128/305, 354, 303, 318; 30/179, 124, 186, 188, 238, 235; 81/43

[56] References Cited

U.S. PATENT DOCUMENTS

| 477,952 | 6/1892 | Moore et al. | 30/135 |
|---|---|---|---|
| 646,633 | 4/1900 | Wiseman | 30/124 |
| 1,491,614 | 4/1924 | Miller | 30/294 |
| 2,069,636 | 2/1937 | Wilson | 128/318 |
| 2,254,738 | 9/1941 | Gamache | 30/175 |
| 2,646,799 | 7/1953 | Jacoby | 30/124 X |
| 3,054,182 | 9/1962 | Whitton | 30/179 |
| 3,336,667 | 8/1967 | Wallace et al. | 30/135 |
| 3,353,531 | 11/1967 | Armao | 30/235 X |
| 3,576,072 | 4/1971 | Foster | 30/124 |
| 3,659,343 | 5/1972 | Straus | 30/124 |
| 3,672,054 | 6/1972 | Kaufman | 30/294 |

FOREIGN PATENT DOCUMENTS

| 1,282,243 | 7/1972 | United Kingdom | 30/124 |

*Primary Examiner*—Robert W. Michell
*Assistant Examiner*—Michael H. Thaler
*Attorney, Agent, or Firm*—Finnegan, Henderson, Farabow & Garrett

[57] ABSTRACT

A disposable suture cutter formed as a resilient member from a single piece of molded material having two opposed free ends to be held between the fingers and thumb. One free end is shaped for insertion in cutting position under a suture without any lateral motion. A suture-retaining groove is positioned on the insertable free end for holding the suture transverse the free end. A cutting blade is attached to the other free end of the resilient member for movement transversely and downwardly relative to the axis of the suture held in the suture-retaining groove. A guide groove is provided on the insertable free end so as to prevent lateral motion of the cutting blade as it is moved across the suture. When operated, the suture cutter slices the suture held in the groove without additional motion of the free insertable end.

5 Claims, 16 Drawing Figures

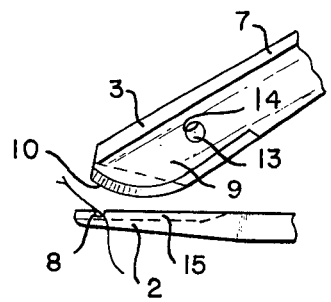
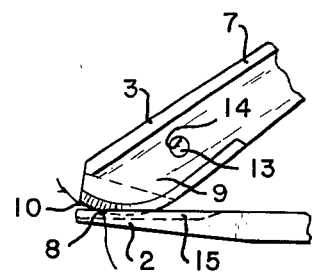
Fig. 5  Fig. 6
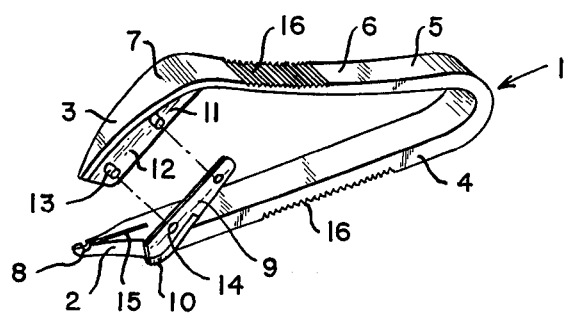
Fig. 7
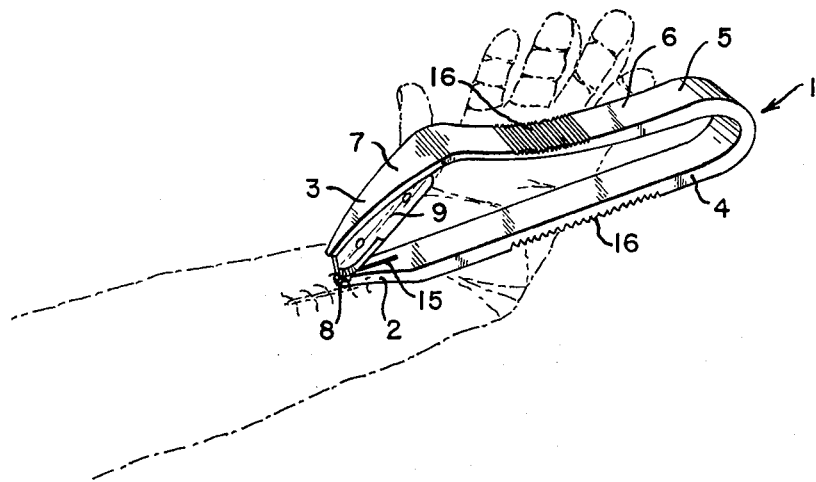
Fig. 8

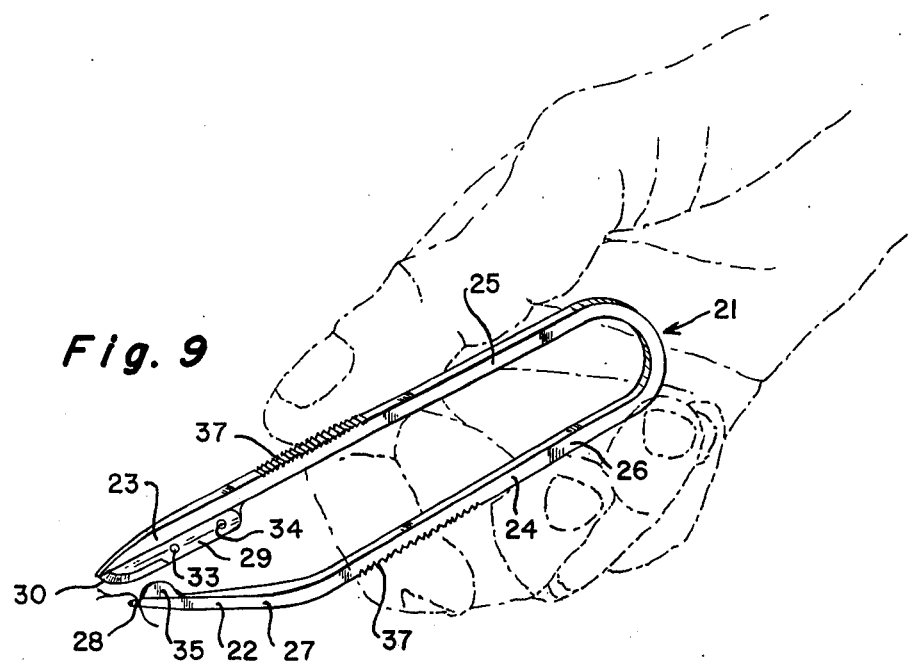
Fig. 9
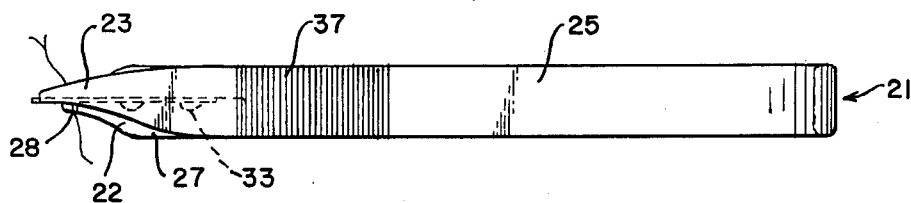
Fig. 11
Fig. 12
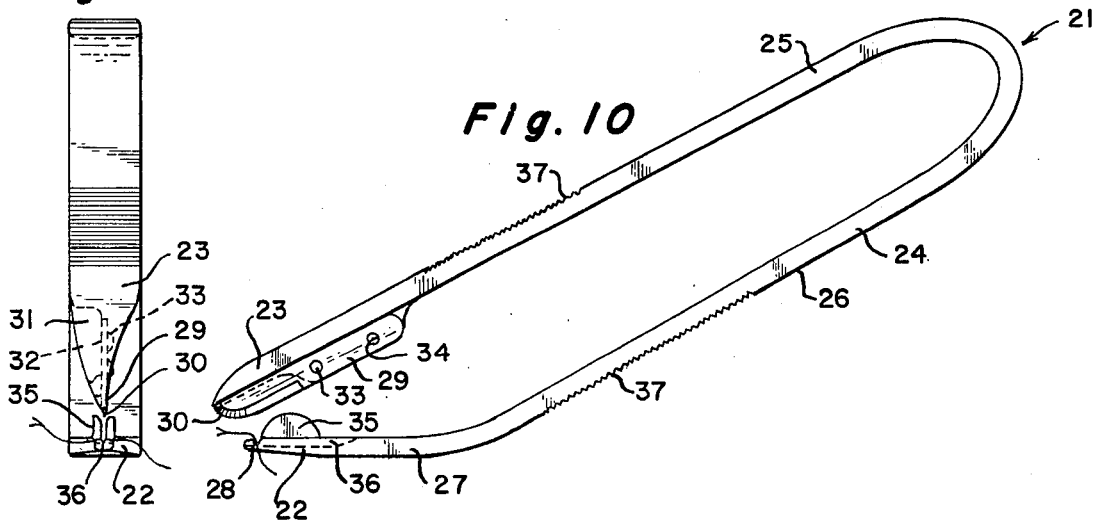
Fig. 10

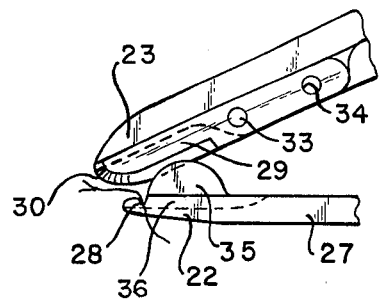
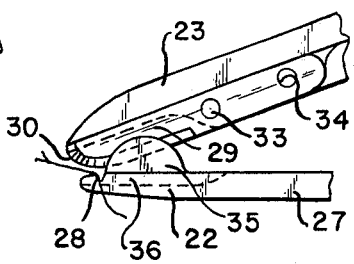
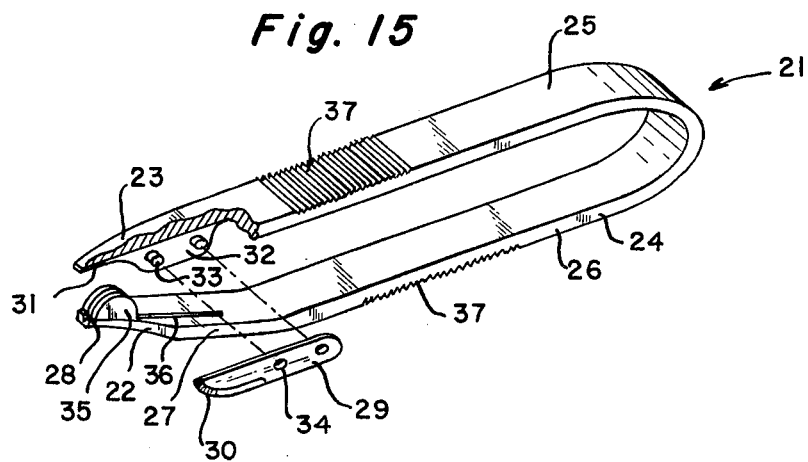
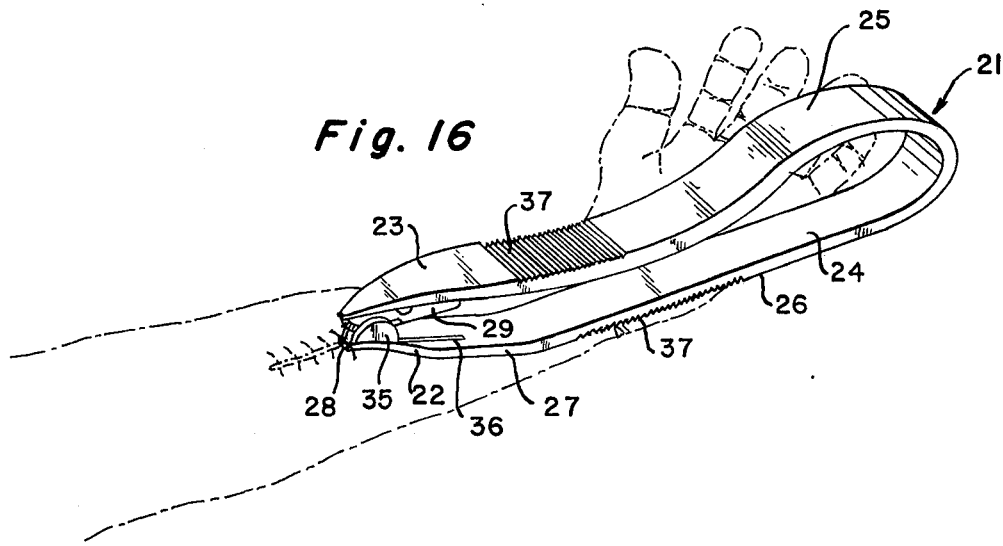

SUTURE CUTTER

The present invention relates to a disposable suture cutter used as a surgical instrument and, more particularly, to a disposable suture cutter for cutting a suture held thereby in a slicing action.

The prior art suture cutters have, in general, been unsatisfactory because the instruments achieve unsatisfactory cutting action on the suture, such as a chopping rather than a slicing action. Most suture cutters of the prior art obtain a slicing action only by an expensive complicated structure, which are not disposable. In order to achieve a slicing action, one suture cutter of relatively simple construction holds the suture in a notch on the side of an inserted shoe, thus requiring that the shoe be moved laterally across the flesh of the patient and against the tightness of the suture into cutting position. Such motion entails undesirable tugging or lifting of the suture from the flesh when severing the suture.

Many suture cutters of the prior art achieve simplified structure by leaving the cutting blade exposed or by utilizing an unstable structure which, for example, permits the elements such as the cutting blade to bend or otherwise become misaligned or do not hold the suture firmly during the cutting operation.

Accordingly, it is an object of this invention to provide a suture cutter for use as a surgical instrument which is disposable and which achieves an accurate and satisfactory cutting of a suture held thereby in a slicing action.

Another object of this invention is to provide a suture cutter which is quickly and easily operated with minimum manual manipulation.

A further object of this invention is to provide a suture cutter which does not require excessive tugging or lifting of the suture from the skin.

Still a further object of this invention is to provide a suture cutter which firmly holds a suture in position during cutting.

Finally, an object of this invention is to provide a suture cutter which has its cutting blade protected for preventing accidental skin puncture.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the foregoing objects and in accordance with the purpose of this invention, as embodied and broadly described herein, the disposable suture cutter of the invention for slicing a suture held thereby comprises (1) a resilient member formed of a single piece of molded material having first and second opposed free ends to be held between the fingers and thumb, the first free end being shaped for insertion in cutting position under a suture without lateral motion, and having a suture-retaining means positioned thereon for holding a suture aligned transversely on the first free end; (2) cutting means attached to the second free end for slicing a suture held in the suture-retaining means without lateral motion of the first free end, the cutting means being movable transversely and downwardly relative to the axis of a suture held in the suture-retaining means; and (3) guiding means on the first free end for preventing lateral motion of the cutting means.

Preferably, the suture cutter described above has the first free end tapered and thin for providing for easy insertion of the tapered first free end under the suture and positioning of the suture in the suture-retaining means.

It is also preferred that the suture-retaining means of the suture cutter be a lateral slot extending across the width of the interior surface of the first free end and that the guiding means for the cutting means include a longitudinal groove intersecting the lateral slot and which has a depth at least equal to or lower than the depth of the lateral slot for ensuring that the cutting means completely and cleanly slices through the suture seated in the lateral slot.

Finally, it is preferred that the suture cutter have first and second elongated arms terminating respectively in the first and second free ends, the second arm being more easily deformable than the first arm.

The invention consists in the novel parts, constructions, arrangements, combinations and improvements shown and described. The accompanying drawings, which are incorporated in and constitute a part of this specification, illustrate embodiments of the invention and, together with the description, serve to explain the principles of the invention.

OF THE DRAWINGS

FIG. 5 is an enlarged side view of the free ends of the disposable suture cutter of FIG. 1 in an opened position;

FIG. 6 is an enlarged side view of the free ends of the disposable suture cutter in a closed position;

FIG. 7 is a perspective view of the disposable suture cutter of FIG. 1 in an as-molded, pre-assembled condition;

FIG. 8 is a perspective view of the disposable suture cutter of FIG. 1 inserted under a suture in a cutting condition;

FIG. 9 is a perspective view of another preferred embodiment of the disposable suture cutter in accordance with the teachings of this invention;

FIG. 10 is a side view of the disposable suture cutter of FIG. 9;

FIG. 11 is a top view of the disposable suture cutter of FIG. 9;

FIG. 12 is a front view of the disposable suture cutter of FIG. 9;

FIG. 13 is an enlarged side view of the free ends of the disposable suture cutter of FIG. 9 in an opened position;

FIG. 14 is an enlarged side view of the free ends of the disposable suture cutter of FIG. 9 in a closed position;

FIG. 15 is a perspective view of the disposable suture cutter of FIG. 9 in an as-molded, pre-assembled condition; and FIG. 16 is a perspective view of the disposable suture cutter of FIG. 9 inserted under a suture in a cutting condition.

Reference will now be made in detail to the present preferred embodiments of the invention, examples of which are illustrated in the accompanying drawings.

Figure 1:
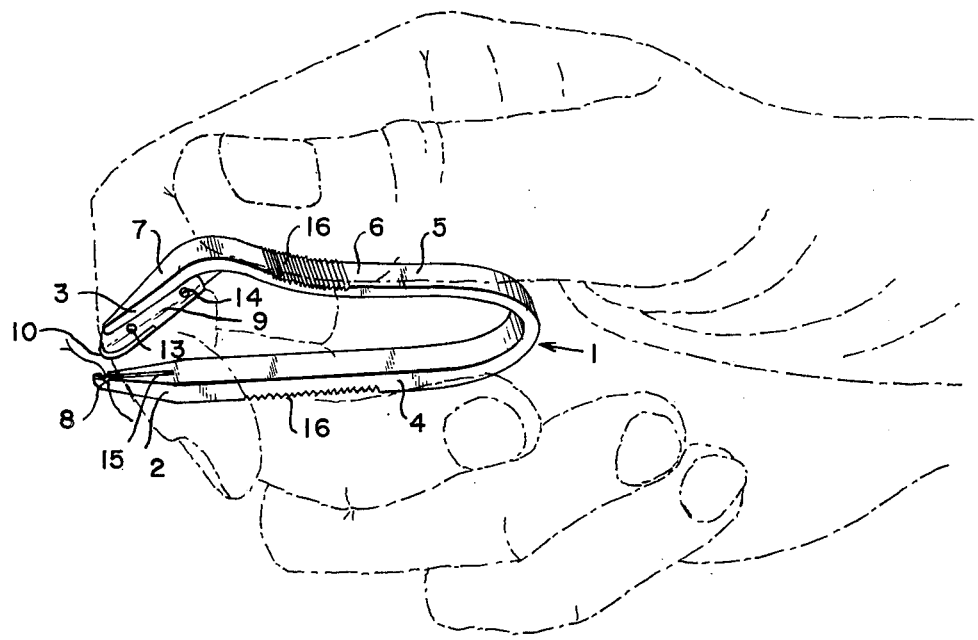
FIG. 1 is a perspective view of one preferred embodiment of the disposable suture cutter in accordance with the teachings of this invention.
Figure 3:
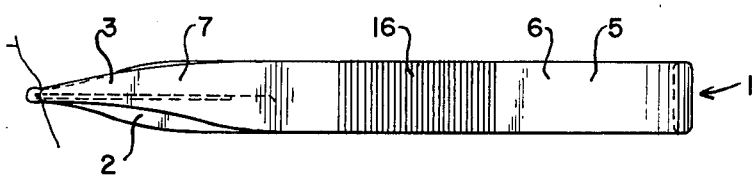
FIG. 3 is a top view of the disposable suture cutter of FIG. 1.
Figure 4:
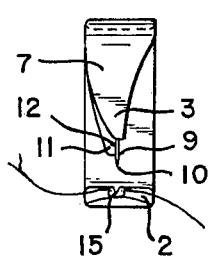
FIG. 4 is a front view of the disposable suture cutter of FIG. 1.
Figure 2:
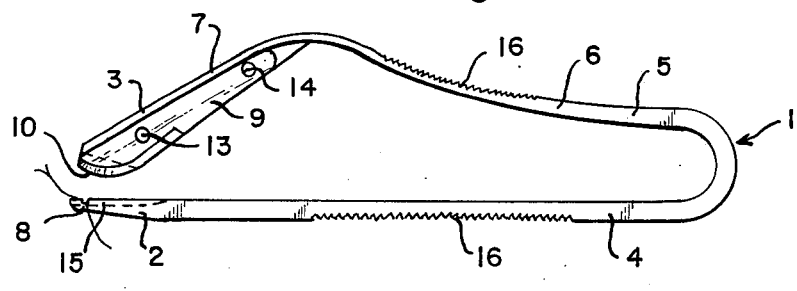
FIG. 2 is a side view of the disposable suture cutter of FIG. 1.

Referring now to FIGS. 1–8, a first preferred embodiment of the disposable suture cutter is shown in accordance with the invention. As seen in FIG. 1, the suture cutter of the invention comprises a resilient member 1 formed of a single piece of molded material having respectively first and second opposed free ends 2 and 3 to be held between the fingers and thumb. As herein embodied, resilient member 1 also includes first and second elongated arms 4 and 5 respectively terminating in first and second free ends 2 and 3. The first and second arms 4 and 5 have end portions opposite the first and second free ends 2 and 3 respectively joined one to the other by a generally semi-circular section as best illustrated in FIG. 2.

In accordance with the invention, the first free end 2 is shaped for insertion in cutting position under a suture without lateral motion. Preferably, the thickness and width of first arm 4 are tapered at first free end 2 for providing easy insertion under the suture and for positioning the suture on first free end 2 without excessively lifting or tugging the suture. As herein embodied, the first arm 4 is substantially planar. The second arm 5, on the other hand, is more easily deformable than first arm 4 and has a first section 6 generally inclined away from first arm 4 and a section 7 inclined inwardly from first section 6 towards first arm 4 to terminate in second free end 3. First section extends generally linearly away from the semicircular arcuate section joining the arms 4 and 5 one to the other while the section 7 extends generally linearly from the first section toward its free end 3. Second free end 3 is aligned at an acute angle to first free end 2 of first arm 4 and is preferably tapered to facilitate an easier viewing of the cutting operation on the suture by the operator.

As here embodied, and best seen in FIG. 2, arms 4 and 5 have roughened areas 16 provided intermediate the ends and on the exterior surface of each of arms 4 and 5 to permit arms 4 and 5 to be firmly grasped during operation of the suture cutter. It is preferred that the roughened area 16 on second arm 5 be located on first section 6 for providing a grasping position for the thumb when operating the suture cutter.

In accordance with the invention, the suture cutter further comprises a suture-retaining means located on first free end 2 for holding the suture to be severed firmly in position transverse first free end 2. As herein embodied, the suture-retaining means is a lateral slot 8 extending across the width of the interior surface of first free end 2 of first arm 4. Preferably, lateral slot 8 is located at the extremity of first free end 2 for ensuring easy and quick insertion of the suture into position in lateral slot 8 without excessively lifting or tugging the suture.

In accordance with the invention, the suture cutter further comprises cutting means attached to second free end 3 for slicing the suture held in the suture-retaining means without lateral motion of first free end 2. The cutting means is movable transversely and downwardly relative to the axis of the suture held in the suture-retaining means. As herein embodied, the cutting means comprises a cutting blade 9 having a convex cutting edge 10. Convex cutting edge 10 is utilized to ensure a slicing action on the suture.

As best seen in FIG. 7, to facilitate attachment of cutting blade 9 and to properly mount cutting blade 9 over first free end 2, it is preferred that second section 7 of second arm 5 have a mounting projection 11 with a planar surface 12 projecting downwardly from the interior surface of second section 7 toward first arm 4. As herein embodied, planar surface 12 has at least one integrally molded boss 13 and cutting blade 9 has at least one hole 14 compatible with boss 13. For assembling cutting blade 9 to planar surface 12, boss 13 extends through hole 14 for mounting blade 9 on the free end 3 and the end of boss 13 is subsequently hot-headed or ultrasonically upset to secure blade 9 thereon. Planar surface 12 is formed to prevent an exposed cutting blade and thus eliminate accidental skin punctures.

Referring again to FIG. 1, in accordance with the invention, the suture cutter also comprises guide means on first free end 2 for preventing lateral motion of the cutting means. The guide means is employed to further ensure an accurate and proper slicing action on the suture. As here embodied, the guiding means is a groove 15 extending longitudinally along a portion of the interior surface of first arm 4 and intersecting lateral slot 8 on a first free end 2. Accordingly, convex cutting edge 10 of cutting blade 9 is aligned over longitudinal groove 15. Preferably, and as best seen in FIG. 5, longitudinal groove 15 has a depth at least equal to the depth of lateral slot 8 so that convex cutting edge 10 completely and cleanly slices through a suture seated in lateral slot 8. It should be noted that the groove 15 need only be of a sufficient width to guide the thin convex cutting edge 10 through lateral slot 8. Consequently, the first free end 2 can be tapered significantly to a thickness and width just sufficient to carry groove 15 and lateral slot 8. This ensures easy insertion and minimizes tugging and lifting of the suture.

Referring to FIG. 1, to operate this first preferred embodiment of the suture cutter, the operator grasps the suture cutter so that the thumb is positioned on the roughened area 16 of second arm 5 while the forefingers are positioned on the roughened area 16 of first arm 4. As best shown in FIG. 5, before pressure is applied on second arm 5 by the thumb, cutting blade 9 is in an inoperative position above first free end 2.

The thin, tapered first free end 2 is then inserted without any lateral motion under a suture for seating the suture in lateral slot 8 in a cutting position. Due to the configuration of first free end 2 and lateral slot 8, insertion under and positioning of the suture is done close to the skin with a minimal amount of tugging and lifting of the suture.

When the suture is properly positioned in lateral slot 8 for cutting, the suture cutter is operated by applying pressure with the thumb on second arm 5. When this is done, second arm 5 moves cutting blade 9 with its convex cutting edge 10 longitudinally in an outward and downward direction through the intersection defined by lateral slot 8 and longitudinal groove 15 as shown in FIGS. 6 and 8. The convex cutting edge 10 of cutting blade 9 is guided through the intersection by longitudinal groove 15 so that no lateral motion of blade 9 occurs during the slicing of the suture.

As the convex cutting edge 10 is guided through the suture by longitudinal groove 15, the suture is sliced accurately, cleanly and completely. This is particularly due to the longitudinal groove 15 having a depth at least equal to the depth of lateral slot 8 so that blade 9 slices the entire thickness of the suture. Also, due to the second arm 5 being more easily deformable than first arm 4, and due to the configuration of second section 7 of second arm 5, the inwardly inclined part of second section 7 of second arm 5 is resiliently flexed to ensure that cutting blade 10 moves outwardly and downwardly in a slicing action across the suture when the pressure is applied by the thumb on the outwardly inclined part of second section 7. When the thumb pressure is released from second arm 5, second arm 5 and second free end 3 return to their original open position due to the resilient material of member 1.

Referring now to FIGS. 9 through 17, a second preferred embodiment of the disposable suture cutter is shown in accordance with the invention. As best seen in FIG. 9, the disposable suture cutter comprises a resilient member 21 being formed of a single piece of molded material having respectively first and second opposed free ends 22 and 23 to be held between the fingers and thumb. As herein embodied, resilient member 21 also includes first and second elongated arms 24 and 25, respectively, terminating in the first and second free ends 22 and 23.

In accordance with the invention, first free end 22 is shaped for insertion in cutting position under a suture without lateral motion. Preferably, the thickness and width of first arm 24 are tapered at first free end 22 for providing easy insertion under the suture and for positioning the suture on first free end 22 without excessively tugging or lifting the suture. As herein embodied, second arm 25 is substantially planar and more easily deformable than first arm 24. First arm 24 has a first section 26 substantially parllel to second arm 25 and a second section 27 inclined inwardly from first section 26 towards second arm 25 to terminate in first free end 22. First free end 22 is aligned at an acute angle to second free end 23 of second arm 25. Preferably, second free end 23 is tapered to facilitate an easier viewing of the cutting operation on the suture by the operator.

As herein embodied, and best seen in FIG. 10, arms 24 and 25 have roughened areas 37 provided intermediate the ends and on the exterior surface of each of arms 24 and 25 to permit arms 24 and 25 to be firmly grasped during operation of the suture cutter. It is preferred that the roughened area 37 on first arm 24 be located on the first section 26 for providing a grasping position for the fingers when operating the suture cutter.

In accordance with the invention, the suture cutter further comprises a suture-retaining means located on first free end 22 for hodling the suture to be severed firmly in position transverse first free end 22. As herein embodied, the suture-retaining means is a lateral slot 28 extending across the width of the interior surface of first free end 22 of first arm 24. Preferably, lateral slot 28 is located at the extremity of first free end 22 for ensuring easy and quick insertion of the suture into position in lateral slot 28 without excessively lifting or tugging the suture.

In accordance with the invention, the suture cutter further comprises cutting means attached to second free end 23 for slicing the suture held in the suture-retaining means without lateral motion of first free end 22. The cutting means is movable transversely and downwardly relative to the axis of the suture held in the suture-retaining means. As herein embodied, the cutting means comprises blade 29 having a convex cutting edge 30. Convex cutting edge 30 is utilized to ensure a slicing action on the suture.

As best seen in FIG. 15, to facilitate attachment of cutting blade 29 and to properly mount cutting blade 29 over first free 22, it is preferred that second arm 25 have a mounting projection 31 with a planar surface 32 projecting downwardly from the interior surface of second arm 25 toward first arm 24. As herein embodied, planar surface 32 has at least one integrally molded boss 33 and cutting blade 28 has at least one hole 34 compatible with boss 33. For assembling cutting blade 29 to planar surface 32, boss 33 extends through hole 34 for mounting blade 29 on the free end 23 and the end of boss 33 is subsequently hot-headed or ultrasonically upset to secure blade 29 thereon. Planar surface 32 is formed to prevent an exposed cutting blade and thus eliminate accidental skin punctures.

Referring again to FIG. 9, in accordance with the invention, the suture cutter also comprises guide means on first free end 22 for preventing lateral motion of the cutting means. The guide means is employed to further ensure an accurate and proper slicing action on the suture. As here embodied, the guiding means is a projection 35 extending upwardly from the interior surface of first free end and rearwardly located with respect to lateral slot 28. Preferably, projection 35 is located immediately adjacent lateral slot 28 and has a groove 36 extending longitudinally therein and outwardly from projection 35 to intersect lateral slot 28 on first free end 22. Accordingly, convex cutting edge 30 of cutting blade 29 is aligned over longitudinal groove 36. Preferably, and as best seen in FIGS. 12-14, longitudinal groove 36 has a depth at least equal to the depth of lateral slot 28 so that convex cutting edge 30 completely and cleanly slices through a suture seated in lateral slot 28. It should be noted that groove need only be of a sufficient width to guide the thin convex cutting edge 30 through lateral slot 28. Consequently, the first free end 22 can be tapered significantly to a thickness an width just sufficient to carry groove and lateral slot 28. This ensures easy insertion and minimizes tugging and lifting of the suture.

Referring to FIG. 9, to operate this second preferred embodiment of the suture cutter, the operator grasps the suture cutter so that the thumb is positioned on the roughened area 37 of second arm 25 while the forefingers are positioned on the roughened area 37 of first arm 24. As best shown in FIG. 10, before pressure is applied on second arm 25 by the thumb, cutting blade 29 is in an inoperative position above first free end 22.

The thin, tapered first free end 22 is then inserted without any lateral motion under a suture for seating the suture in lateral slot 28 in a cutting position. Due to the configuration of first free end 22 and lateral slot 28, insertion under and positioning of the suture is done close to the skin with a minimal amount of tugging and lifting of the suture.

When the suture is properly positioned in lateral slot 28 for cutting, the suture cutter is operated by applying pressure with the thumb on a second arm 25. When this is done, second arm 25 moves cutting blade 29 with its convex cutting edge 30 longitudinally in a rearward and downward direction through the intersection defined by lateral slot 28 and longitudinal groove 36 as shown in FIGS. 13, 14 and 16. The convex cutting edge 30 of cutting blade 29 is guided through the intersection by projection 35 so that no lateral motion of blade 30 occurs during the slicing of the suture.

As the convex cutting edge 30 is guided through the suture by projection 35, the suture is sliced accurately, cleanly and completely. This is particularly due to the longitudinal groove 36 having a depth at least equal to the depth of lateral slot 28 so that blade 29 slices the entire thickness of the suture. Also, due to the second arm 25 being more easily deformable than first arm 24, second arm 25 is resiliently flexed to ensure that cutting blade 30 moves rearwardly and downwardly in a slicing action across the suture when the pressure is applied by the thumb on second arm 25. When the thumb pressure is released from second arm 25, second arm 25 and second free end 23 return to their original open position due to the resilient material of member 21.

It will be apparent to those skilled in the art that various modifications and variations could be made in the disposable suture cutter of the invention without departing from the scope or spirit of the invention.

What is claimed is:

1. A disposable suture cutter for slicing a suture held thereby comprising:

a resilient member including first and second elongated arms terminating respectively in first and second opposed free ends and adapted to be held between the fingers and thumb respectively, said first free end being shaped for insertion in cutting position under a suture without lateral motion;

suture retaining means carried by said first free end for holding a suture aligned transversely on said first free end including a lateral slot for seating the suture extending across the full width of the interior surface of said first free end in opposition to said second free end and inwardly of the tip of said first free end;

cutting means carried by said second free end and including a cutting blade having a longitudinally extending convex edge for slicing a suture held by said suture retaining means without lateral motion of said first free end; and guide means on said first free end for preventing lateral motion of said cutting means including a groove extending longitudinally along a portion of the interior surface of said first arm and intersecting said lateral slot on said first free end, said groove of said first free end lying in aligned opposition to the cutting blade carried by said second free end, said longitudinal grove and said blade lying in a common plane substantially medially of the width of said arms, said second arm being movable without lateral motion toward said first arm to move said cutting blade toward said first free end in a direction transverse to the axis of a suture held in said lateral slot and being deformable when bearing against said first arm to move said cutting blade longitudinally parallel to said groove through the intersection of said slot and said groove to slice the suture held by said suture retaining means when pressure is exerted to displace said second arm toward said first arm and deform said second arm against said first arm, said first and second arms having end portions opposite their free ends, a generally semi-circular section connecting said opposite end portions of said arms one to the other, said first arm being substantially planar and extending generally linearly; said second arm having a generally linearly extending first section generally inclined away from said first arm and extending from said semi-circular section, said second arm having a generally linearly extending second section inclined inwardly from said first section toward said first arm to terminate in said second free end aligned at an acute angle to said first free end, said second section having a mounting projection with a planar surface for mounting said cutting blade; said second section being movable transversely and downwardly relative to the axis of a suture held in said lateral slot to move said cutting edge of said blade longitudinally in a direction toward the tip of said first free end.

2. The disposable suture cutter of claim 1 wherein said planar surface of said mounting projection has at least one integrally molded boss, said cutting blade having a hole, said boss extending through said hole for mounting said blade on said boss.

3. The disposable suture cutter of claim 1 wherein said second section terminates in a tapered second free end to permit an operator to view said cutting blade as it slices the suture during operation of said suture cutter.

4. The disposable suture cutter of claim 1 wherein each of said arms has a roughened area intermediate its ends and on its exterior surface to permit said arms to be firmly grasped during operation of said suture cutter.

5. The disposable suture cutter of claim 4 wherein the roughened surface on said second arm is located on said first section for providing a grasping position of said second arm when operating said suture cutter.

* * * * *

UNITED STATES PATENT AND TRADEMARK OFFICE
CERTIFICATE OF CORRECTION

PATENT NO. : 4,053,979
DATED : October 18, 1977
INVENTOR(S) : Harlan L. Tuthill and John O. Freeborn It is certified that error appears in the above-identified patent and that said Letters Patent are hereby corrected as shown below:

At column 7, line 50 change "grove" to --groove--.

Signed and Sealed this

Seventh Day of February 1978

[SEAL]

Attest:

RUTH C. MASON
Attesting Officer

LUTRELLE F. PARKER
Acting Commissioner of Patents and Trademarks